(12) United States Patent
Igarashi

(10) Patent No.: US 10,758,664 B2
(45) Date of Patent: *Sep. 1, 2020

(54) BIOLOGICAL COMPONENT COLLECTION SYSTEM AND CIRCUIT INTERNAL PRESSURE ACQUISITION METHOD

(71) Applicant: TERUMO KABUSHIKI KAISHA, Tokyo (JP)

(72) Inventor: Masatsugu Igarashi, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/668,572

(22) Filed: Oct. 30, 2019

(65) Prior Publication Data
US 2020/0164135 A1 May 28, 2020

(30) Foreign Application Priority Data

Nov. 1, 2018 (JP) .................................. 2018-206645

(51) Int. Cl.
*A61M 1/36* (2006.01)
*A61M 1/34* (2006.01)
(Continued)

(52) U.S. Cl.
CPC ........ *A61M 1/3693* (2013.01); *A61M 1/0272* (2013.01); *A61M 1/3496* (2013.01);
(Continued)

(58) Field of Classification Search
CPC .............. A61M 1/3693; A61M 1/0209; A61M 1/0272; A61M 1/3496; A61M 2205/3331;
(Continued)

(56) References Cited

U.S. PATENT DOCUMENTS 6,280,406 B1    8/2001   Dolecek et al.
6,491,656 B1 * 12/2002   Morris ................ A61M 1/3621
                                                                  604/6.09

(Continued)

FOREIGN PATENT DOCUMENTS

EP            0214803 A2    3/1987
WO    WO-2004061399 A2 *   7/2004  ......... A61M 1/3639

(Continued)

OTHER PUBLICATIONS

International Searching Authority and Written Opinion, PCT/JP2019/041298, dated Jan. 23, 2020, 13 pages.

*Primary Examiner* — Charles Cooley
(74) *Attorney, Agent, or Firm* — Terumo BCT, Inc IP Law Dept

(57) ABSTRACT

A centrifugal separation device of a blood component collection system comprises a data acquisition unit that acquires initial data A, an estimated data calculation unit that calculates estimated data B on the basis of the initial data A, a reaction force calculation unit which calculates a reaction force of a first applied load measurement unit on the basis of the estimated data B, and an internal pressure calculation unit that calculates an internal pressure of the first applied load measurement unit, based on the reaction force and a load detected by a first load detecting unit.

4 Claims, 14 Drawing Sheets

(51) Int. Cl.
*A61M 1/02* (2006.01)
*B04B 13/00* (2006.01)
*B04B 7/02* (2006.01)
*G16H 10/40* (2018.01)
*B04B 5/04* (2006.01)
*B04B 11/04* (2006.01)

(52) U.S. Cl.
CPC .......... *B04B 5/0428* (2013.01); *B04B 5/0442* (2013.01); *B04B 7/02* (2013.01); *B04B 11/04* (2013.01); *B04B 13/00* (2013.01); *G16H 10/40* (2018.01); *A61M 2202/0415* (2013.01); *A61M 2205/332* (2013.01); *A61M 2205/3331* (2013.01); *A61M 2205/50* (2013.01)

(58) Field of Classification Search
CPC ...... A61M 2205/50; A61M 2202/0415; A61M 2205/332; B04B 11/04; B04B 7/08; B04B 11/00; B04B 2005/0435; B04B 5/0428; B04B 7/02; B04B 13/00; B04B 5/0442; G16H 10/40
See application file for complete search history.

(56) References Cited

U.S. PATENT DOCUMENTS

| | | | |
|---|---|---|---|
| 10,352,950 B2 * | 7/2019 | Ochiai | G01N 21/27 |
| 10,413,653 B2 * | 9/2019 | Case | A61M 1/3639 |
| 2002/0107468 A1 | 8/2002 | Chevallet et al. | |
| 2010/0152013 A1 * | 6/2010 | Eberle | B04B 5/0428 494/10 |
| 2010/0292628 A1 * | 11/2010 | Powers | A61M 1/3639 604/6.01 |
| 2011/0152055 A1 | 6/2011 | Pittinger et al. | |
| 2016/0243300 A1 * | 8/2016 | Nackaerts | A61M 1/3693 |
| 2019/0038197 A1 * | 2/2019 | Igarashi | A61B 5/150251 |
| 2019/0046710 A1 * | 2/2019 | Kusters | A61M 1/306 |
| 2019/0231949 A1 * | 8/2019 | Igarashi | A61M 1/0236 |
| 2019/0290822 A1 * | 9/2019 | Igarashi | A61M 1/267 |
| 2019/0290825 A1 * | 9/2019 | Igarashi | A61M 1/38 |
| 2019/0290830 A1 * | 9/2019 | Igarashi | A61M 1/3607 |
| 2019/0290831 A1 * | 9/2019 | Igarashi | B04B 11/02 |
| 2020/0164135 A1 * | 5/2020 | Igarashi | B04B 5/0442 |
| 2020/0164136 A1 * | 5/2020 | Igarashi | A61M 1/0218 |
| 2020/0164137 A1 * | 5/2020 | Igarashi | B04B 5/0442 |
| 2020/0197582 A1 * | 6/2020 | Igarashi | A61M 1/302 |
| 2020/0197583 A1 * | 6/2020 | Igarashi | A61M 1/30 |

FOREIGN PATENT DOCUMENTS

| | | | | |
|---|---|---|---|---|
| WO | 2011084348 A2 | 7/2011 | | |
| WO | WO-2018230155 A1 * | 12/2018 | ............ | A61M 1/302 |
| WO | WO-2018230156 A1 * | 12/2018 | ............ | A61M 1/302 |
| WO | WO-2018230545 A1 * | 12/2018 | .......... | A61M 1/0218 |

* cited by examiner

BIOLOGICAL COMPONENT COLLECTION SYSTEM AND CIRCUIT INTERNAL PRESSURE ACQUISITION METHOD

TECHNICAL FIELD

The present invention relates to a biological component collection system equipped with a biological component collection device configured to be attachable to a separation device, as well as to a circuit internal pressure acquisition method.

BACKGROUND ART

In blood donation in recent years, in addition to whole blood collection in which whole blood is collected from a blood donor, component blood sampling (apheresis) has been performed in which the burden on the blood donor's body is made lighter. Component blood sampling is a blood collection method in which a blood component collection system (apheresis system) is used, whereby only specific blood components are collected from whole blood, and the remaining components are returned again into the donor's body.

In Patent Document 1, a blood component collection system is disclosed in which blood platelets are collected by centrifugally separating whole blood that is extracted from a blood donor. Such a blood component collection system comprises a blood collection circuit set, which forms a circuit through which blood or blood components to be treated flow, and a centrifugal separation device (blood component separation device) in which the blood collection circuit set is mounted.

The blood collection circuit set is equipped with a plurality of bags for accommodating a blood collection line having a blood collection needle, a band-shaped channel (separator) into which whole blood is introduced, and the blood components, etc., and a cassette connected through a plurality of tubes to the bags. A plurality of flow paths, including a line for introducing blood from a blood donor, a line for transferring the blood components into a bag, a blood returning line for returning uncollected blood components to the donor, etc., are formed in the cassette. When used, the cassette is mounted in a mounting unit disposed in the blood component separation device.

PRIOR ART DOCUMENTS

Patent Documents

Patent Document 1
Published Japanese Translation of PCT International Application No. 2013-514863 (WO2011/084348).

SUMMARY OF INVENTION

Problems the Invention Aims to Solve

In the blood component collection system, in order to ascertain whether or not the blood component separation device is operating properly, it is necessary to measure and monitor the pressure (circuit internal pressure) inside the blood collection circuit. Similar problems also occur in biological component collection systems other than blood component collection systems.

The present invention has been devised taking into consideration the aforementioned problems, and has the object of providing a biological component collection system and a circuit internal pressure acquisition method, which are capable of accurately measuring the circuit internal pressure.

Means for Solving the Problem

One aspect of the present invention relates to a biological component collection system equipped with a separation device adapted to separate a biological component from a biological liquid, and a biological component collection device configured to be attachable to the separation device and collect a desired biological component from the biological liquid, wherein the biological component collection device is formed of a soft material and has a line forming member defining a biological liquid line to allow the biological liquid or the biological component to flow therein, the separation device comprising a load detecting unit adapted to detect a load applied to an applied load measurement unit which partially makes up the line forming member in a device installed state in which the biological component collection device is attached to the separation device, a data acquisition unit adapted to acquire, before the biological liquid or the biological component is made to flow through the biological liquid line for biological component collection, initial data indicative of a timewise change in a reaction force of the load measurement unit using the load detected by the load detecting unit in the device installed state, an estimated data calculation unit adapted to calculate, on the basis of the initial data, estimated data for estimating the reaction force of the load measurement unit which changes over time during collection of the biological component, a reaction force calculation unit adapted to calculate, during collection of the biological component, the reaction force on the basis of the estimated data, and an internal pressure calculation unit adapted to calculate an internal pressure of the load measurement unit, on the basis of the reaction force calculated by the reaction force calculation unit and the load detected by the load detecting unit.

Another aspect of the present invention relates to a circuit internal pressure acquisition method using a biological component collection system equipped with a separation device adapted to separate a biological component from a biological liquid, and a biological component collection device configured to be attachable to the separation device and collect a desired biological component from the biological liquid, wherein the biological component collection device is formed of a soft material and has a line forming member defining a biological liquid line to allow the biological liquid or the biological component to flow therein, the separation device comprising a load detecting unit adapted to detect a load applied to an applied load measurement unit which partially makes up the line forming member in a device installed state in which the biological component collection device is attached to the separation device, wherein the circuit internal acquisition method comprises a data acquisition step of acquiring, before the biological liquid or the biological component is made to flow through the biological liquid line for biological component collection, initial data indicative of a timewise change in a reaction force of the load measurement unit using the load detected by the load detecting unit in the device installed state, an estimated data calculation step of calculating, on the basis of the initial data, estimated data for estimating the reaction force of the load measurement unit which changes over time during collection of the biological component, a reaction force calculation step of calculating, during collection of the biological component, the reaction force on the basis of the estimated data, and an internal pressure calculation step of calculating an internal pressure of the load measurement unit, on the basis of the reaction force calculated by the reaction force calculation unit and the load detected by the load detecting unit.

Effects of the Invention

According to the present invention, since based on the estimated data it is possible to calculate the reaction force of the applied load measurement unit during collection of biological components which change with the passage of time, it is possible for the circuit internal pressure to be accurately measured.

DESCRIPTION OF EMBODIMENTS

Preferred embodiments of a biological component collection system and a circuit internal pressure acquisition method according to the present invention will be presented and described in detail below with reference to the accompanying drawings.

Figure 1:
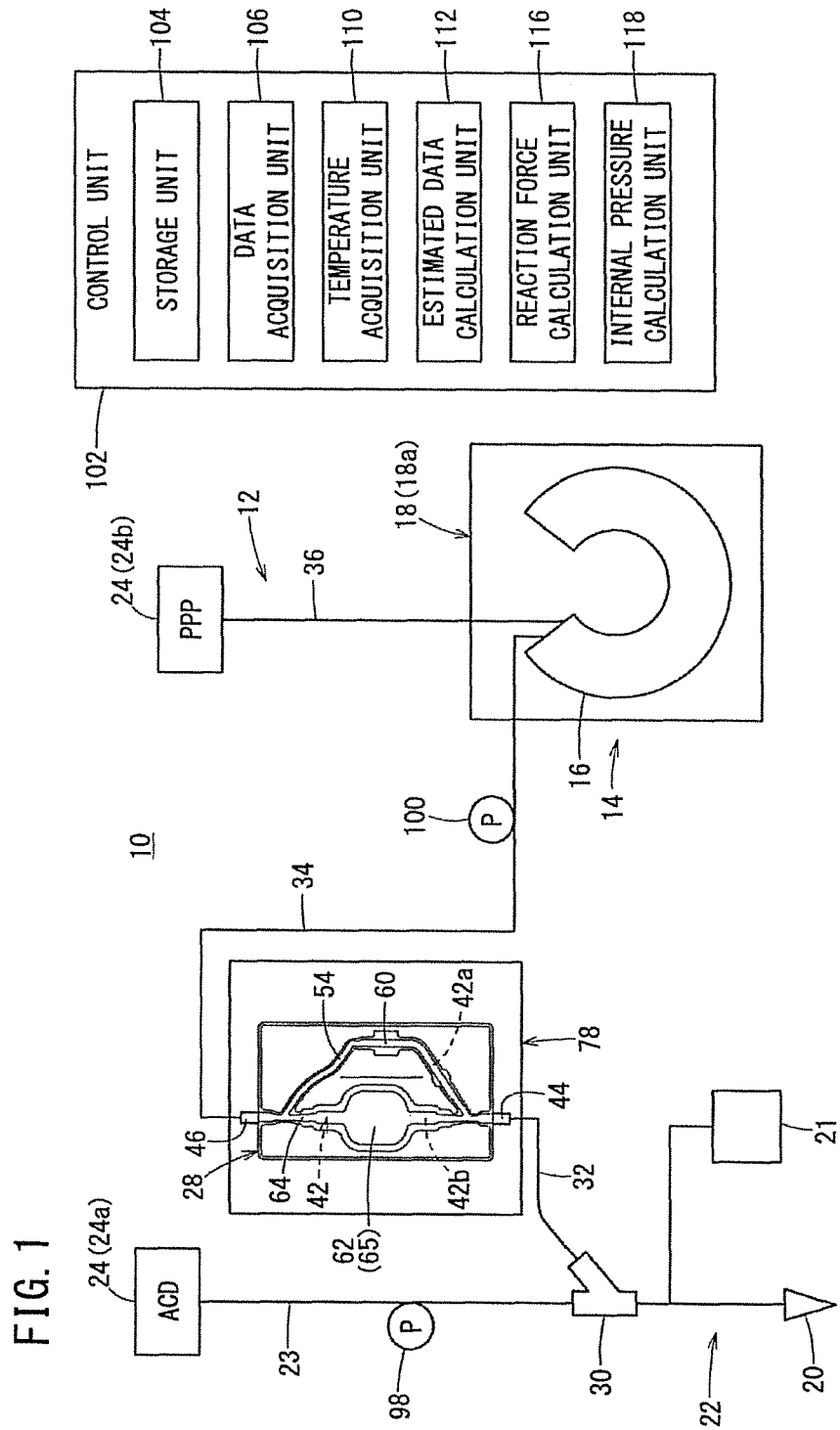
FIG. 1 is a schematic diagram of a blood component collection system according to an embodiment of the present invention.

As shown in FIG. 1, a blood component collection system 10, which is one form of a biological component collection system according to the present invention, is constituted as a blood apheresis system, in which blood (whole blood) is continuously extracted from a blood donor and subjected to centrifugal separation outside the body, whereby a specific blood component (in the present embodiment, plasma (platelet poor plasma: PPP)) is collected, and the remaining blood components are returned to the blood donor. In the present embodiment, the blood component is a biological component, and the blood is a biological liquid (a liquid containing at least one biological component).

First, an outline description will be given of the blood component collection system 10 shown in FIG. 1. The blood component collection system 10 is equipped with a blood collection circuit set 12 for enabling storage and flow of blood components therein, and a centrifugal separation device 14 (separation device) that applies a centrifugal force to the blood collection circuit set 12. The blood collection circuit set 12 includes a blood treatment unit 16 (biological liquid treatment unit) in which whole blood that is removed from the blood donor is centrifugally separated into a plurality of blood components. The centrifugal separation device 14 is equipped with a centrifuge unit 18 having a rotor 18a for applying a centrifugal force to the blood treatment unit 16. The blood treatment unit 16 is capable of being mounted in the centrifuge unit 18.

The blood collection circuit set 12 is discarded every time that it is used in order to prevent contamination and ensure sanitation. The blood collection circuit set 12 includes a blood collecting and blood returning unit 22 having a blood collecting needle 20 and an initial flow blood collecting bag 21, a blood treatment unit 16, a plurality of bags 24, and a blood component collection cassette 28 (hereinafter referred to as a "cassette 28") serving as a biological component collection device to which the aforementioned elements are connected via tubes. The plurality of bags 24 include an ACD solution bag 24a containing an ACD solution which is an anticoagulant, and a PPP bag 24b for storing the plasma (platelet poor plasma).

The blood collecting and blood returning unit 22 is connected to the ACD solution bag 24a and the cassette 28 via a tube connector 30. The ACD solution bag 24a is connected to the tube connector 30 via an ACD solution transfer tube 23.

The cassette 28 is connected to the blood collecting and blood returning unit 22 via a donor side tube 32, and is also connected to the blood treatment unit 16 via a treatment unit side tube 34. The blood treatment unit 16 is attached to the centrifuge unit 18 (rotor 18a) of the centrifugal separation device 14, and is configured in the form of a container in which blood can be introduced therein, flow therethrough, and flow out therefrom. The PPP bag 24b is connected to the blood treatment unit 16 via a PPP transfer tube 36.

Figure 2:
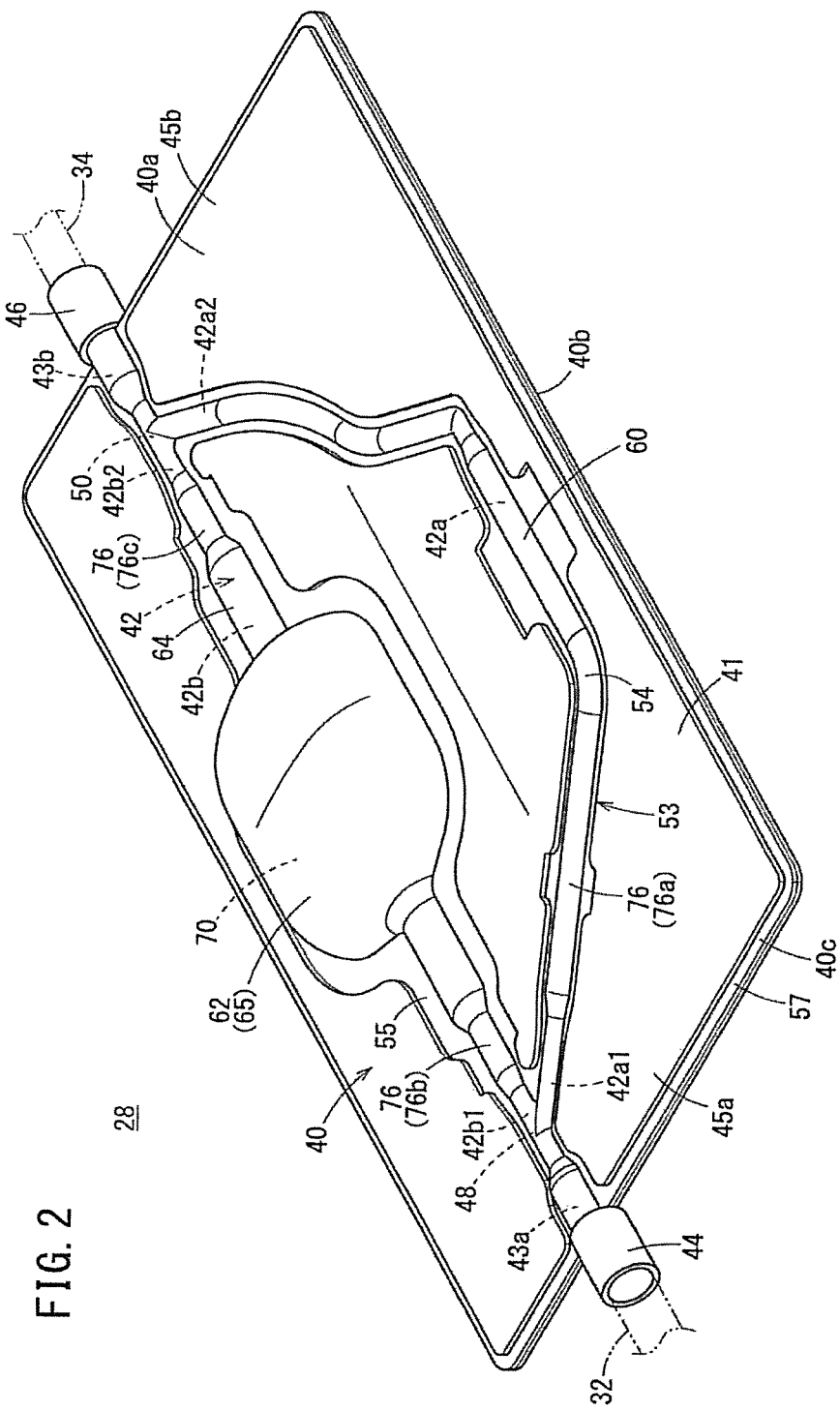
FIG. 2 is a perspective view of a blood component collection cassette.

As shown in FIG. 2, the cassette 28 is provided with a cassette body 40 in which a blood line 42 (biological liquid line) is formed through which blood or blood components flow. The cassette body 40 is formed in a rectangular shape as viewed in plan. The cassette body 40 is formed of a soft material. For the soft material that constitutes the cassette body 40, the same material is used over the entirety of the cassette body 40. Moreover, the cassette body 40 may be constituted from a plurality of different materials. More specifically, the cassette body 40 includes a first sheet 40a and a second sheet 40b formed of a soft material. The first sheet 40a and the second sheet 40b are stacked in a thickness direction and are joined to each other.

As examples of the soft material that constitutes the first sheet 40a and the second sheet 40b, there may be cited vinyl chloride, polyolefin, polyurethane, and the like. As examples of a vinyl chloride plasticizer, there may be cited diisononylcyclohexane-1,2-dicarboxylate, bis-2-ethylhexyl phthalate, and the like.

The blood line 42 is formed between the first sheet 40a and the second sheet 40b. In the present embodiment, fusion bonding (high frequency fusion bonding, thermal fusion bonding, etc.) is used as the means for joining the first sheet 40a and the second sheet 40b. The first sheet 40a and the second sheet 40b may also be joined together by another joining means (adhesion or the like). Further, a first port member 44 and a second port member 46, which are made of a hard material (for example, polypropylene, polycarbonate, or the like), are disposed on an outer peripheral edge portion 40c of the cassette body 40.

The first port member 44 is provided at a first end portion 45a, which is one longitudinal end portion of the rectangular cassette body 40, and is connected to a first port 43a provided on one end side of the blood line 42. The second port member 46 is provided at a second end portion 45b, which is another longitudinal end portion of the cassette body 40, and is connected to a second port 43b provided on the other end side of the blood line 42. The donor side tube 32 is connected to the first port member 44, and the treatment unit side tube 34 is connected to the second port member 46.

According to the present embodiment, the first port member 44 and the second port member 46 are arranged on the same straight line along the longitudinal direction of the rectangular cassette body 40. Moreover, the first port member 44 and the second port member 46 need not necessarily be arranged on the same straight line.

The blood line 42 which is formed in the cassette body 40 includes a blood collection line 42a (collection line) through which the blood is made to flow at a time of blood collection, and a blood returning line 42b (returning line) through which the blood components are made to flow at a time that the blood is returned. One end portion 42a1 of the blood collection line 42a and one end portion 42b1 of the blood returning line 42b are connected mutually via a first coupling member 48. Another end portion 42a2 of the blood collection line 42a and another end portion 42b2 of the blood returning line 42b are connected mutually via a second coupling member 50.

The blood collection line 42a and the blood returning line 42b extend at least partially in parallel with each other. The first coupling member 48 and the second coupling member 50 each constitute parts of the blood line 42.

In the cassette body 40, sealed portions 55 in the form of fusion-bonded locations are formed along the blood line 42 on both sides of the blood line 42. Further, a sealed portion 57 is formed along the outer peripheral edge portion 40c, on the outer peripheral edge portion 40c of the cassette body 40. In the cassette body 40 (excluding the convex portion that forms the blood line 42), locations other than the sealed portions 55 and 57 are non-sealed portions where the first sheet 40a and the second sheet 40b are not fusion bonded to each other. Since the sealed portions 55 are subject to pressure during formation thereof, the sealed portions 55 are smaller in thickness than the non-sealed portions, and are recessed with respect to the non-sealed portions. Stated otherwise, the non-sealed portions protrude in the thickness direction with respect to the sealed portions 55.

In the cassette body 40, even when there is no positive pressure acting within the blood line 42, the wall portions that form the blood line 42 bulge in convex shapes in the thickness direction of the cassette 28 on both side surfaces of the cassette body 40. Accordingly, the blood line 42 is a flow path which is opened in its natural state. When pressed by an external force, the wall portions can be elastically deformed in directions to close the blood line 42 at the pressed locations thereof.

The cassette body 40 comprises a line forming member 53 that forms the blood line 42. The line forming member 53 includes a first line forming member 54 that forms the blood collection line 42a. In the first line forming member 54, in a cassette attached state (device attached state) in which the cassette 28 is attached to the centrifugal separation device 14, a first applied load measurement unit 60 (first pressed portion) is provided, which is pressed by a later-described first load detecting unit 88 (see FIG. 3) that is installed in the centrifugal separation device 14. The first applied load measurement unit 60 constitutes a part of the wall portions of the blood collection line 42a. Accordingly, the first applied load measurement unit 60 bulges out in the thickness direction of the cassette body 40 from a sheet surface 41 (base surface) of the cassette body 40.

The line forming member 53 includes a second line forming member 64 that forms a blood returning line 42b. In the second line forming member 64, in the cassette attached state, a second applied load measurement unit 62 (second pressed portion) is provided, which is pressed by a later-described second load detecting unit 90 (see FIG. 3) that is installed in the centrifugal separation device 14. The second applied load measurement unit 62 constitutes a part of the wall portions of the blood returning line 42b. Accordingly, the second applied load measurement unit 62 bulges out in the thickness direction of the cassette body 40 from a sheet surface 41 of the cassette body 40.

The second applied load measurement unit 62 constitutes a filter accommodating unit 65. The filter accommodating unit 65 accommodates a filter member 70 for separating predetermined components (clotted blood or blood clumps) contained within the blood components.

The second applied load measurement unit 62 is more easily deformable than the first applied load measurement unit 60. In the present embodiment, the width of the second applied load measurement unit 62 is greater than the width of the first applied load measurement unit 60, whereby the second applied load measurement unit 62 is more easily deformable than the first applied load measurement unit 60. The ratio of the width of the second applied load measurement unit 62 with respect to the width of the first applied load measurement unit 60 is set, for example, to 300% or greater, preferably is set to 500% or greater, and more preferably, is set to 800% or greater.

Moreover, the width of the wall portion that constitutes the second applied load measurement unit 62 may be set to be thinner than the width of the wall portion of the first applied load measurement unit 60, whereby the second applied load measurement unit 62 may be more easily deformable than the first applied load measurement unit 60. Alternatively, the second applied load measurement unit 62 may be made of a material that is softer than that of the first applied load measurement unit 60, whereby the second applied load measurement unit 62 may be more easily deformable than the first applied load measurement unit 60.

On the cassette 28, there are provided a plurality of clamp action members 76 (76a to 76c) on which a plurality of clamps 72 (72a to 72c) (see FIG. 3), which act as flow path opening/closing mechanisms, are provided in the centrifugal separation device 14. When the cassette 28 is installed in the centrifugal separation device 14, the clamp action members 76 abut against or are placed in facing relation to their corresponding clamps 72. More specifically, the clamp action member 76a is disposed at a location forming a side of the first port member 44 of the blood collection line 42a in the cassette 28. The clamp action members 76b, 76c are disposed respectively at locations forming both sides of the second applied load measurement unit 62 within the blood returning line 42b.

Moreover, the flow path structure formed in the cassette 28, and the number and arrangement of the bags 24 that are provided are not limited to the configurations shown and described above, but may be modified in accordance with the type of blood components to be collected, the method of use, and the like.

In FIG. 1, the centrifugal separation device 14 is a device that is used repeatedly during blood component collection, and is provided, for example, in a medical facility, a blood collection vehicle, or the like. The centrifugal separation device 14 is equipped with the centrifuge unit 18 having the rotor 18a, and a cassette mounting unit 78 configured in a manner so that the cassette 28 of the blood collection circuit set 12 is capable of being attached thereto.

Figure 3:
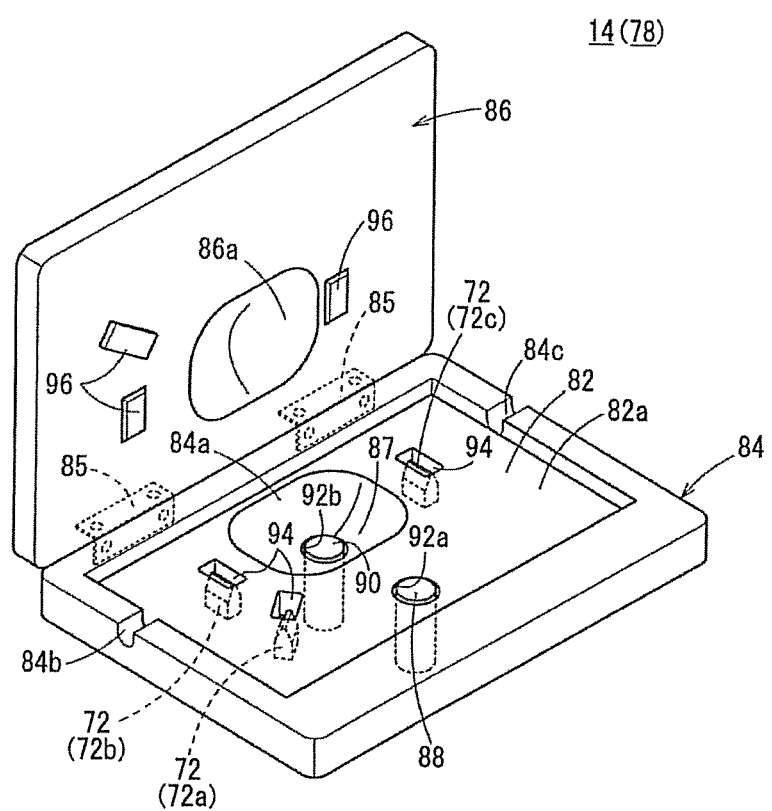
FIG. 3 is a perspective view of a cassette mounting unit.

As shown in FIG. 3, the cassette mounting unit 78 includes an attachment base 84 having a cassette mounting groove 82 formed therein, a lid 86 which can be opened and closed and is configured in a manner so as to cover the attachment base 84 when closed, a first load detecting unit 88 capable of pressing the first applied load measurement unit 60 (see FIG. 2) of the cassette 28, a second load detecting unit 90 capable of pressing the second applied load measurement unit 62 (see FIG. 2) of the cassette 28, and a plurality of clamps 72 configured to be capable of pressing the clamp action members 76 (see FIG. 2) of the cassette 28.

A first port arrangement groove 84b into which the first port member 44 of the cassette 28 can be arranged, and a second port arrangement groove 84c into which the second port member 46 of the cassette 28 can be arranged are provided on the outer peripheral portion of the attachment base 84. The first port arrangement groove 84b and the second port arrangement groove 84c are in communication with the cassette mounting groove 82.

The lid 86 is connected in a rotatable manner to the attachment base 84 via a hinge 85. When the lid 86 is closed with the cassette 28 being held in the cassette mounting groove 82 of the attachment base 84, the cassette 28 is sandwiched between the attachment base 84 and the lid 86. On the attachment base 84 and the lid 86, there are respectively provided concave portions 84a, 86a in which the filter accommodating unit 65 of the cassette 28 can be received. Consequently, the cassette 28 is appropriately retained between the attachment base 84 and the lid 86, while also preventing the filter accommodating unit 65 from being crushed. Further, the concave portions 84a, 86a prevent the filter accommodating unit 65 from bulging excessively.

The first load detecting unit 88 is inserted into a first through hole 92a provided in the attachment base 84, together with being exposed in the cassette mounting groove 82. An upper surface of the first load detecting unit 88 protrudes from a bottom surface 82a of the cassette mounting groove 82. The second load detecting unit 90 is inserted into a second through hole 92b provided in a bottom surface 87 of the concave portion 84a, together with being exposed in the concave portion 84a. An upper surface of the second load detecting unit 90 protrudes from the bottom surface 87 of the concave portion 84a. The first load detecting unit 88 and the second load detecting unit 90 are constituted from load cells, for example.

The plurality of clamps 72 (72a to 72c) are capable of being advanced and retracted in the thickness direction of the cassette 28 in a state in which the cassette 28 is retained in the cassette mounting groove 82, and are disposed corresponding to the arrangement of the plurality of clamp action members 76 (76a to 76c) provided on the cassette 28. The plurality of clamps 72 are capable of pressing the plurality of clamp action members 76, respectively, via a plurality of holes 94 that open on a bottom surface 82a of the cassette mounting groove 82. When closed, a plurality of projections 96 are provided on the lid 86 at positions corresponding to the plurality of holes 94 (clamps 72).

At a time that the clamp action members 76 are not being pressed by the clamps 72, in a state in which the cassette 28 is mounted in the cassette mounting unit 78, the flow paths inside the clamp action members 76 are opened. When the clamps 72 protrude from the holes 94 and press the clamp action members 76, the flow paths inside the clamp action members 76 are closed. In addition, when the clamps 72 are retracted, due to the elastic restorative force of (the clamp action members 76 of) the cassette body 40, the clamp action members 76 are restored to their original shape, and the flow paths inside the clamp action members 76 are opened.

As shown in FIG. 1, the centrifugal separation device 14 includes an ACD solution transfer pump 98 which acts on the ACD solution transfer tube 23, and a collection and returning pump 100 which acts on the treatment unit side tube 34 that is connected to the cassette 28. The ACD solution transfer pump 98 is a pump that transfers the ACD solution from the ACD solution bag 24a to the cassette 28 and the blood treatment unit 16 via the ACD solution transfer tube 23. The collection and returning pump 100 is a pump for transferring blood or blood components. Stated otherwise, the collection and returning pump 100 is a pump that transfers blood from the blood donor to the blood treatment unit 16, and together therewith, transfers the blood from the blood treatment unit 16 back to the blood donor. The ACD solution transfer pump 98 and the collection and returning pump 100 are constituted, for example, by a roller pump or a finger pump.

The centrifugal separation device 14 further includes a control unit 102. The control unit 102 is a computation device including a microcomputer, and has a CPU (central processing unit), and a ROM, a RAM, etc., serving as memories, wherein by reading out and executing programs stored in the ROM, the CPU functions as various function realizing units (function realizing means). Moreover, the various function realizing units may be constituted by function realizing devices in the form of hardware.

The control unit 102 controls operations of the above-described plurality of clamps 72. The control unit 102 comprises a storage unit 104, a data acquisition unit 106, a temperature acquisition unit 110, an estimated data calculation unit 112, a reaction force calculation unit 116, and an internal pressure calculation unit 118.

Figure 11:
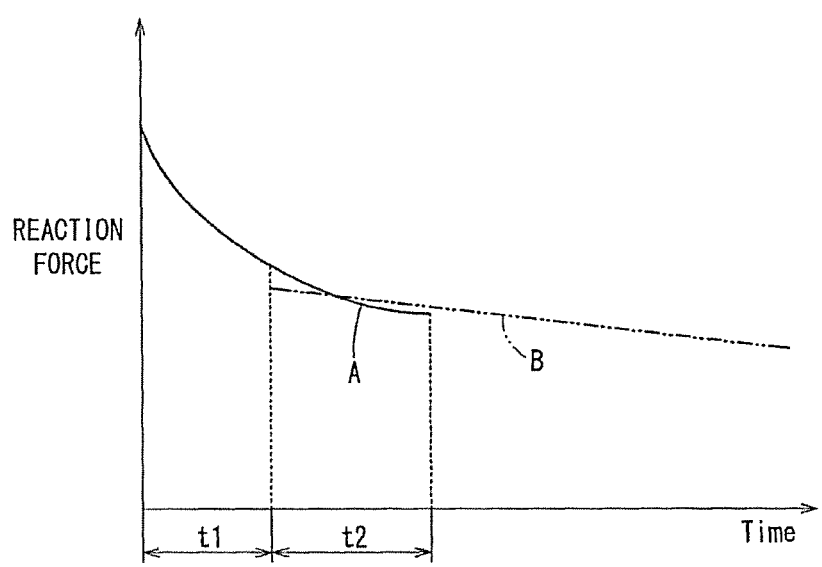
FIG. 11 is a graph for describing estimated data.

Before collection of blood components during which blood or blood components are made to flow in the blood line 42 in the cassette attached state, the data acquisition unit 106 acquires initial data A indicative of a temporal change in the reaction force of the first applied load measurement unit 60 (see FIG. 11). The temperature acquisition unit 110 (information acquisition unit) acquires the temperature of the line forming member 53 (influence information that exerts an influence on the reaction force of the first applied load measurement unit 60).

On the basis of the initial data A, the estimated data calculation unit 112 calculates estimated data B (see FIG. 11) for the purpose of estimating the reaction force of the first applied load measurement unit 60 during collection of the blood components. More specifically, the estimated data calculation unit 112 calculates the estimated data B using a least squares method based on the initial data A. During collection of the blood components, the reaction force calculation unit 116 calculates the reaction force of the first applied load measurement unit 60 based on the estimated data B.

During collection of the blood components, the internal pressure calculation unit 118 calculates the internal pressure (circuit internal pressure) of the first applied load measurement unit 60, on the basis of the reaction force of the first applied load measurement unit 60 as calculated by the reaction force calculation unit 116, and the load detected by the first load detecting unit 88. More specifically, when calculating the internal pressure of the first applied load measurement unit 60, the internal pressure calculation unit 118 carries out a calculation that reflects a change in the reaction force of the first applied load measurement unit 60 due to temperature.

Next, operations of the blood component collection system 10 according to the present embodiment, which is configured in the manner described above, will be described.

As a preparation (set-up) for collecting blood components from a blood donor using the blood component collection system 10 shown in FIG. 1, the blood collection circuit set 12 is attached to the centrifugal separation device 14. More specifically, the cassette 28 is mounted in the cassette mounting unit 78, and the blood treatment unit 16 is attached to the rotor 18a. On the other hand, the blood collecting needle 20 pierces and is inserted into the blood donor.

Figure 4:
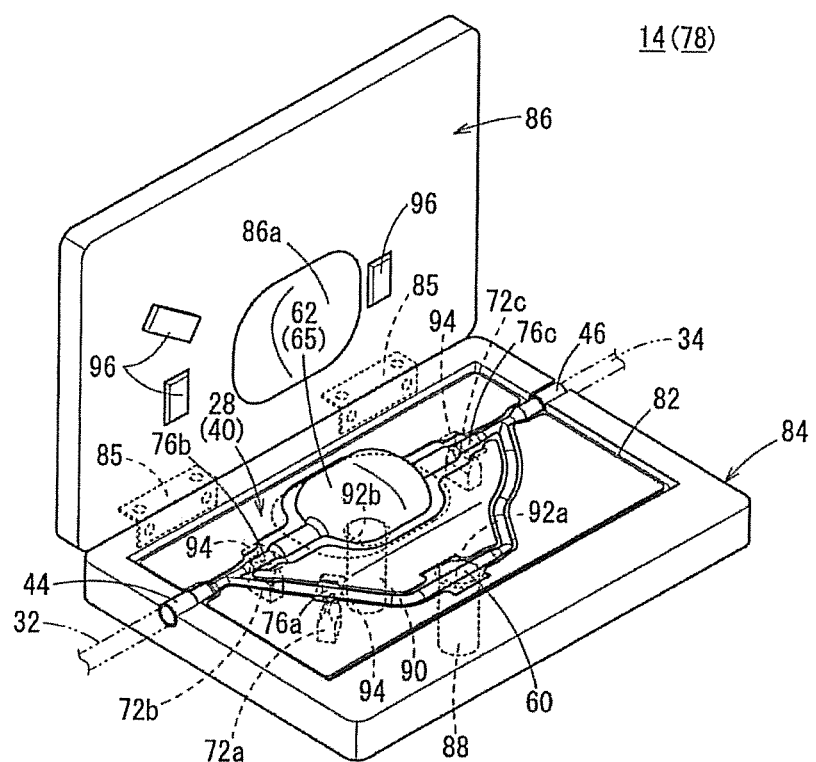
FIG. 4 is a perspective view of a cassette mounting unit in a state with the blood component collection cassette placed therein.

When the cassette 28 is mounted in the cassette mounting unit 78, as shown in FIG. 4, at first, the cassette 28 is mounted in the cassette mounting groove 82. In addition, by closing the lid 86, the cassette 28 is placed in a state of being held between the lid 86 and the attachment base 84. As a result, the first applied load measurement unit 60 and the second applied load measurement unit 62 of the cassette 28 are pressed respectively by the first load detecting unit 88 and the second load detecting unit 90, and are placed in a state of being slightly elastically deformed. Further, the plurality of clamp action members 76 of the cassette 28 are placed in facing relation with respect to the plurality of clamps 72.

When a command is issued by operation of a user with respect to the centrifugal separation device 14 shown in FIG. 1 in order to initiate operations, in the centrifugal separation device 14, under the action of the ACD solution transfer pump 98, priming with the ACD solution is carried out. More specifically, at a stage at which it is detected by a non-illustrated line sensor disposed outside of the cassette 28 that the ACD solution has arrived in the immediate vicinity of the first port 43a, priming by the ACD solution is terminated.

Next, by rotating the rotor 18a, the centrifugal separation device 14 applies a centrifugal force to the blood treatment unit 16 that is attached to the rotor 18a, and together therewith, by operation of the collection and returning pump 100, blood (whole blood) from the blood donor is extracted and introduced into the blood treatment unit 16 (blood collection operation). By the centrifugal force that accompanies rotation of the rotor 18a, the blood introduced into the blood treatment unit 16 is separated into red blood cells (concentrated red blood cells), a buffy coat, and plasma (platelet poor plasma).

The plasma that is separated in the blood treatment unit 16 is introduced into the PPP bag 24b via the PPP transfer tube 36. After completion of the centrifugal separation process, the remaining blood components (the red blood cells and the buffy coat) are returned to the blood donor (returning operation). At this time, since foreign substances such as blood clumps and the like contained within the remaining blood components are trapped by the filter member 70 provided in the blood returning line 42b of the cassette 28, any risk of such foreign matter being returned to the blood donor can be reduced. The collection operation and the returning operation described above are performed a plurality of times.

During operation of the blood component collection system 10, the clamps 72 (see FIG. 3) of the centrifugal separation device 14 are operated in the following manner.

Figure 5:
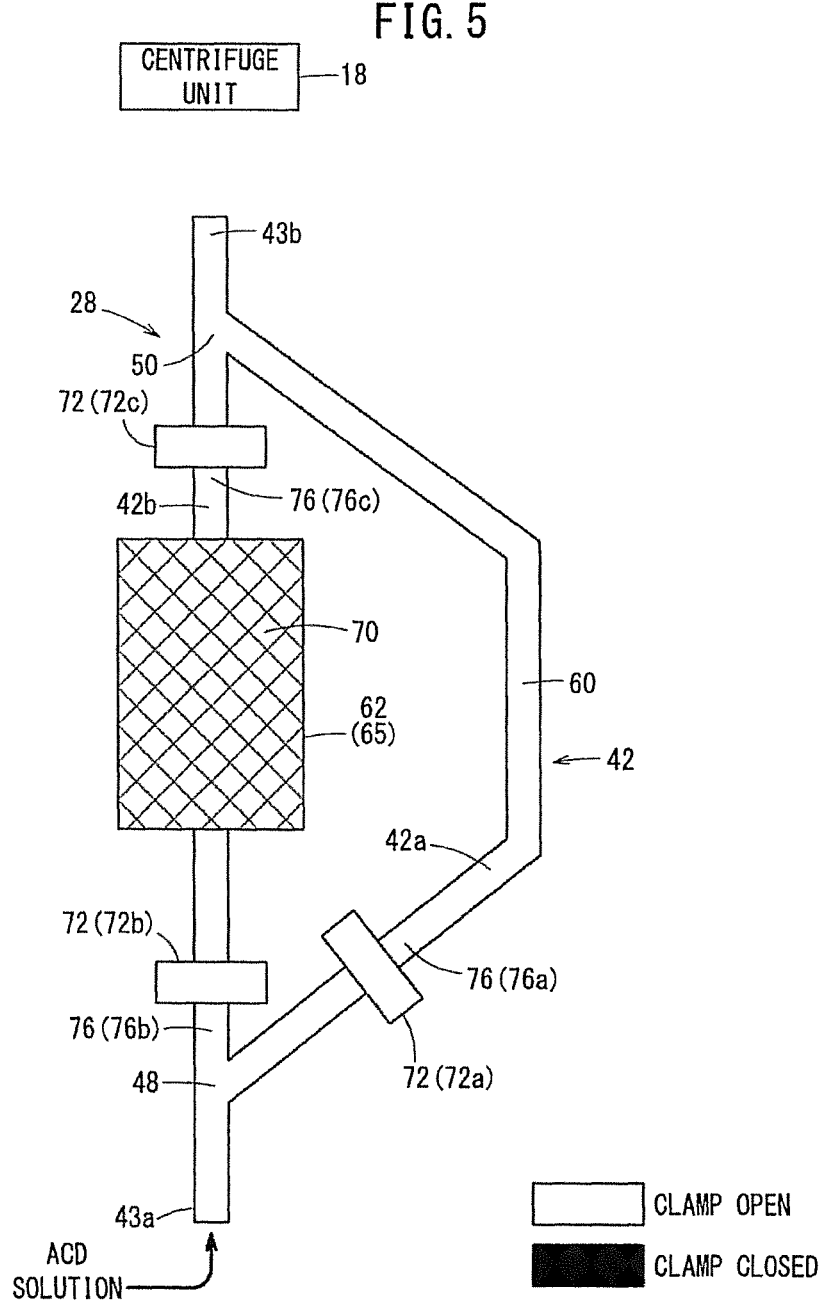
FIG. 5 is a first explanatory diagram illustrating the operation of clamps.

As shown in FIG. 5, when priming by the ACD solution is carried out, the clamps 72a, 72b, and 72c are opened. In addition, in this state, priming by the ACD solution is terminated at a stage at which it is detected by a non-illustrated line sensor outside the cassette 28 in the immediate vicinity of the first port 43a that the ACD solution has arrived in close proximity to the first port 43a.

Figure 6:
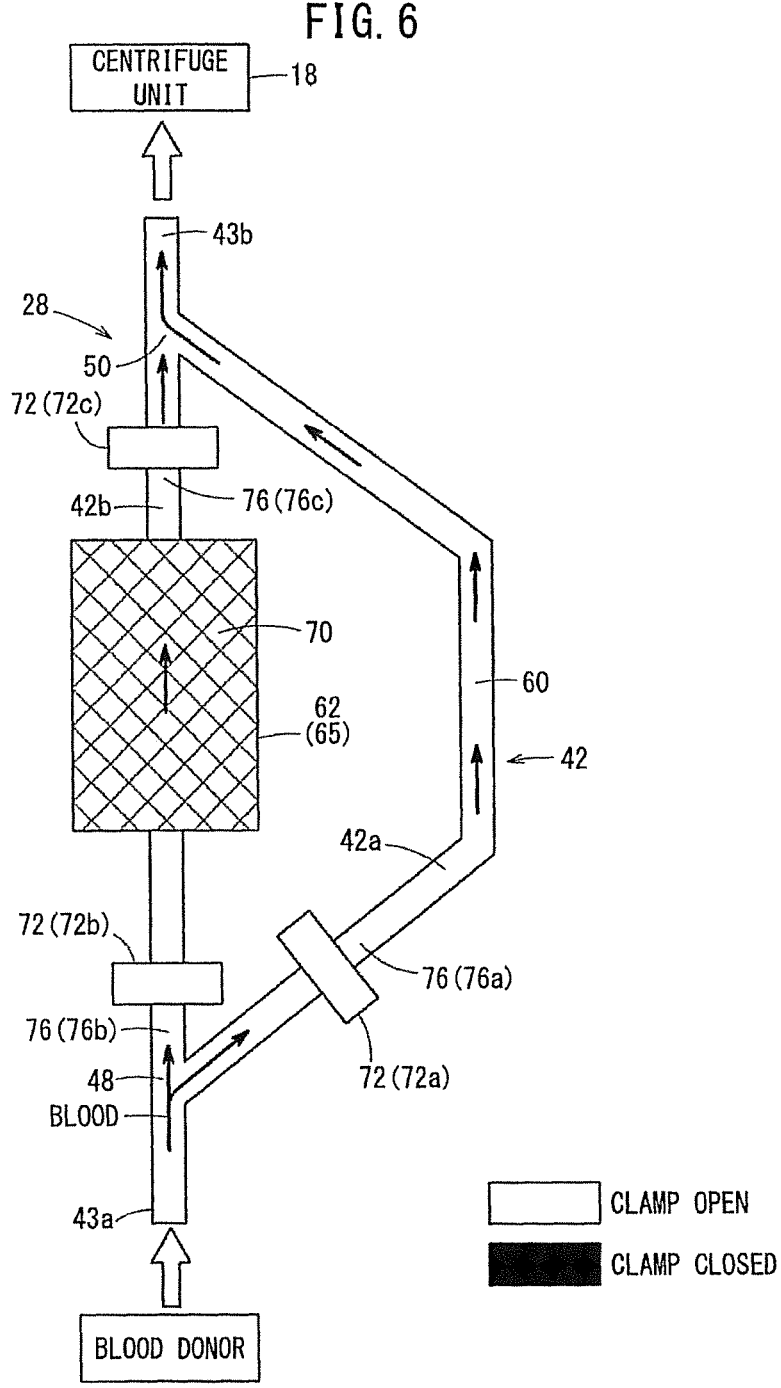
FIG. 6 is a second explanatory diagram illustrating the operation of clamps.

Next, when blood collection is performed for the first time, as shown in FIG. 6, the state in which the clamps 72a, 72b, and 72c are opened is maintained. In addition, in this state, blood from the blood donor is introduced into the blood line 42 of the cassette 28, and all of the air inside the circuit of the cassette 28 is pushed out by the blood into the blood treatment unit 16.

Figure 7:
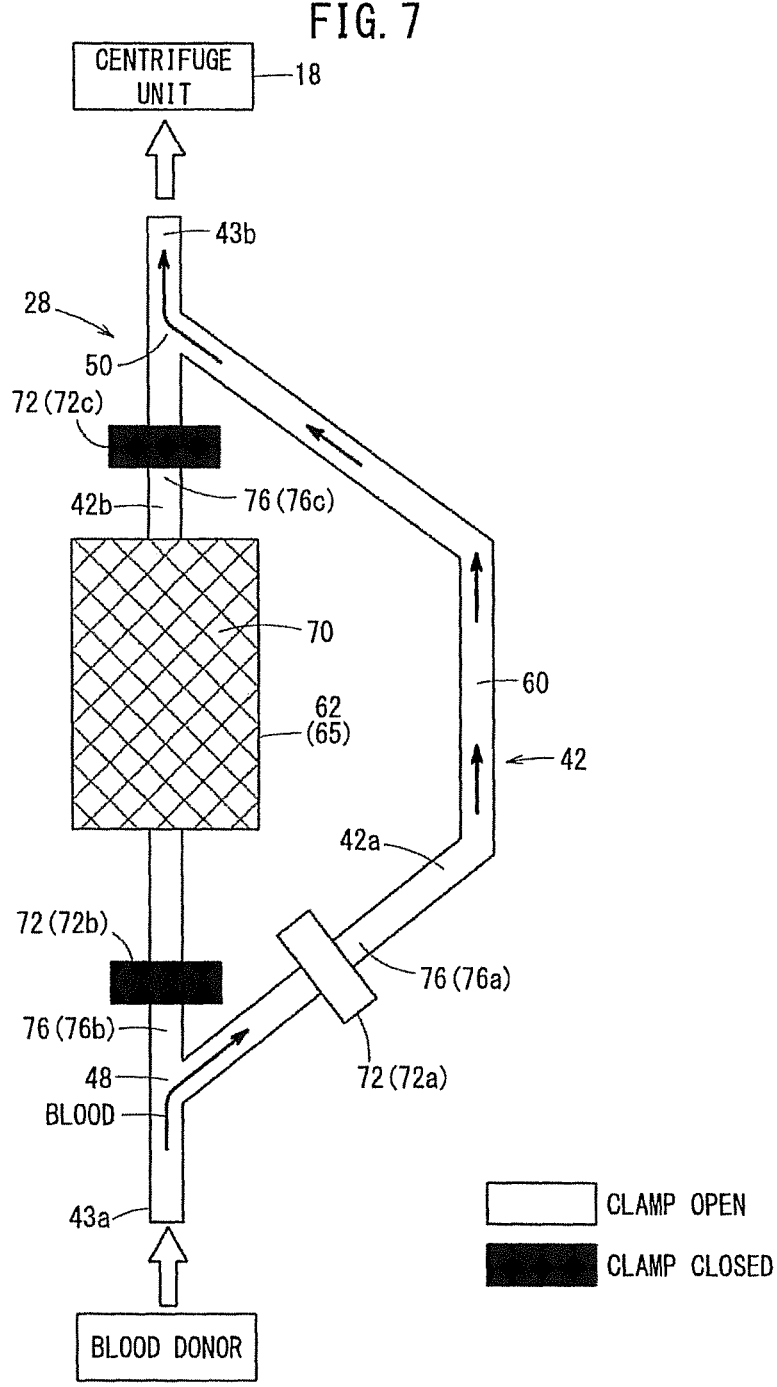
FIG. 7 is a third explanatory diagram illustrating the operation of clamps.

During the course of initial blood collection, as shown in FIG. 7, by closing the clamps 72b and 72c, the blood returning line 42b is closed. Consequently, a negative pressure is prevented from acting on the filter accommodating unit 65 and blocking the filter accommodating unit 65.

Figure 8:
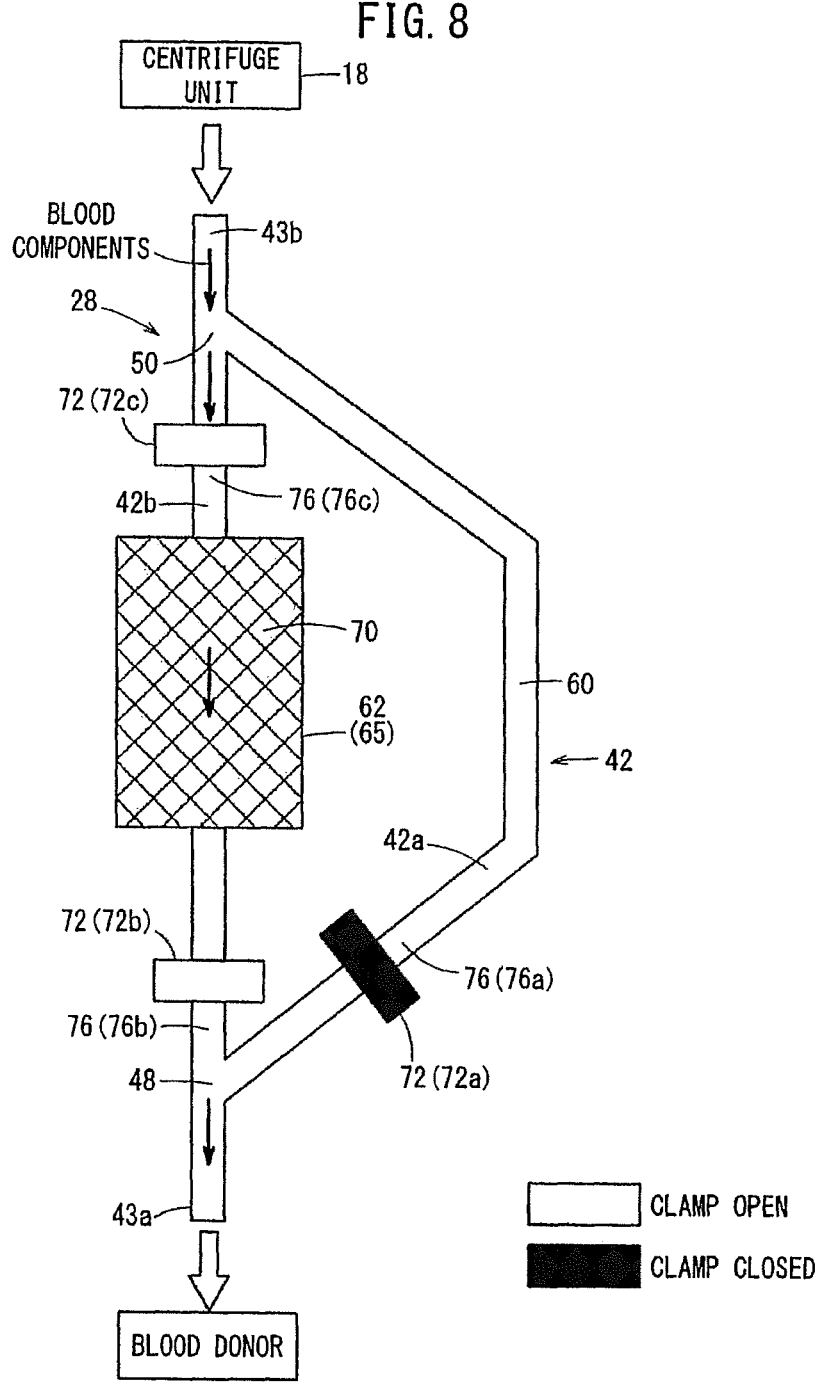
FIG. 8 is a fourth explanatory diagram illustrating the operation of clamps.

Next, when return of the blood components to the blood donor is carried out, as shown in FIG. 8, the clamp 72a is closed, and the clamps 72b and 72c are opened. Thus, the blood collection line 42a is closed, whereas the blood returning line 42b is opened. Accordingly, when the blood components pass through the filter member 70, clotted blood contained within the blood components is trapped in the filter member 70. Since the blood collection line 42a is closed, foreign matter cannot be returned to the blood donor via the blood collection line 42a.

Figure 9:
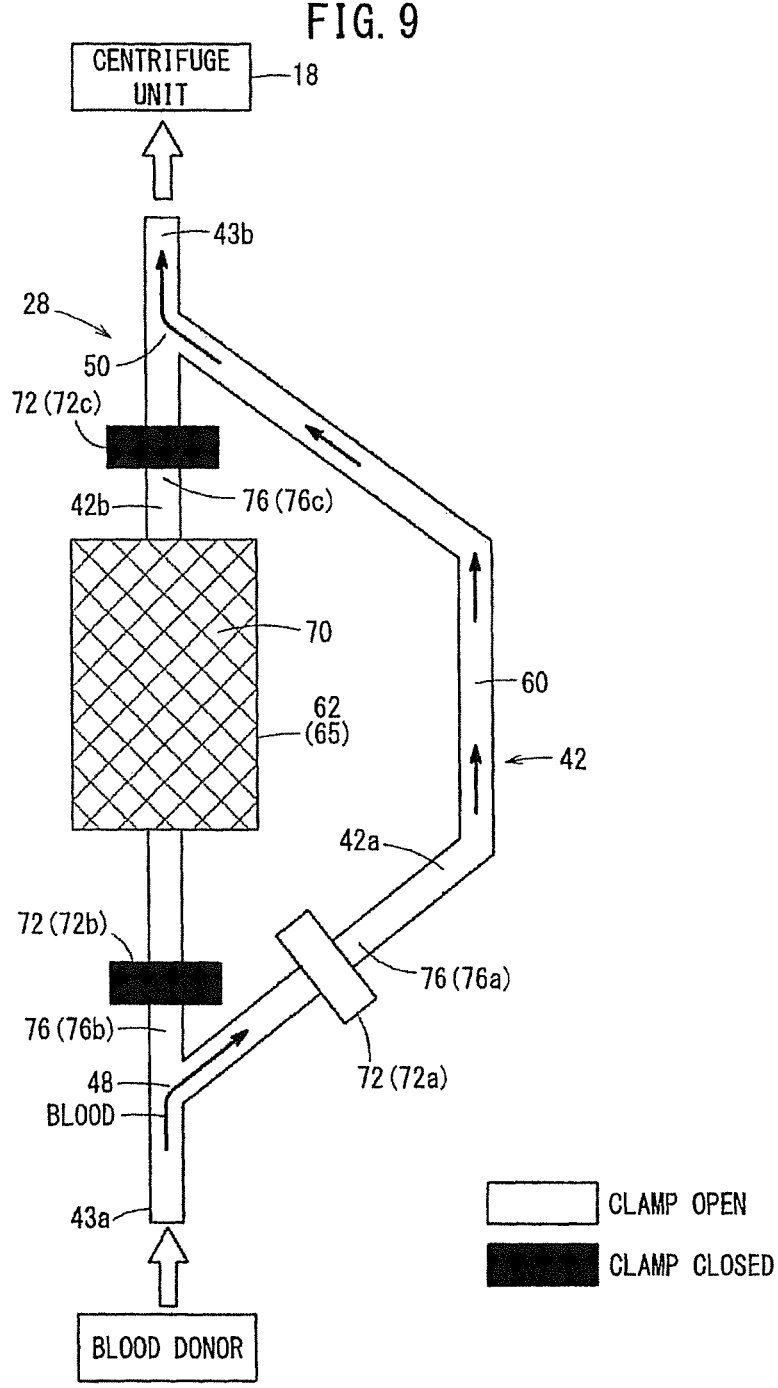
FIG. 9 is a fifth explanatory diagram illustrating the operation of clamps.

Next, when second and subsequent blood collections are carried out, as shown in FIG. 9, the clamps 72b and 72c are closed, and the clamp 72a is opened. Thus, the blood returning line 42b is closed, whereas the blood collection line 42a is opened. Accordingly, from among the blood collection line 42a and the blood returning line 42b, blood is transferred via only the blood collection line 42a to (the centrifuge unit 18 of) the blood treatment unit 16. Thereafter, return of the blood (see FIG. 8) is carried out again. Collection of blood and return of the blood in this manner are repeated a plurality of times.

In addition, when return of the blood is performed for the last time, as shown in FIG. 8, the clamp 72a is closed, and the clamps 72b and 72c are opened.

Next, a circuit internal pressure acquisition method in which the blood component collection system 10 is used will be described with reference to the flowchart shown in FIG. 10.

Figure 10:
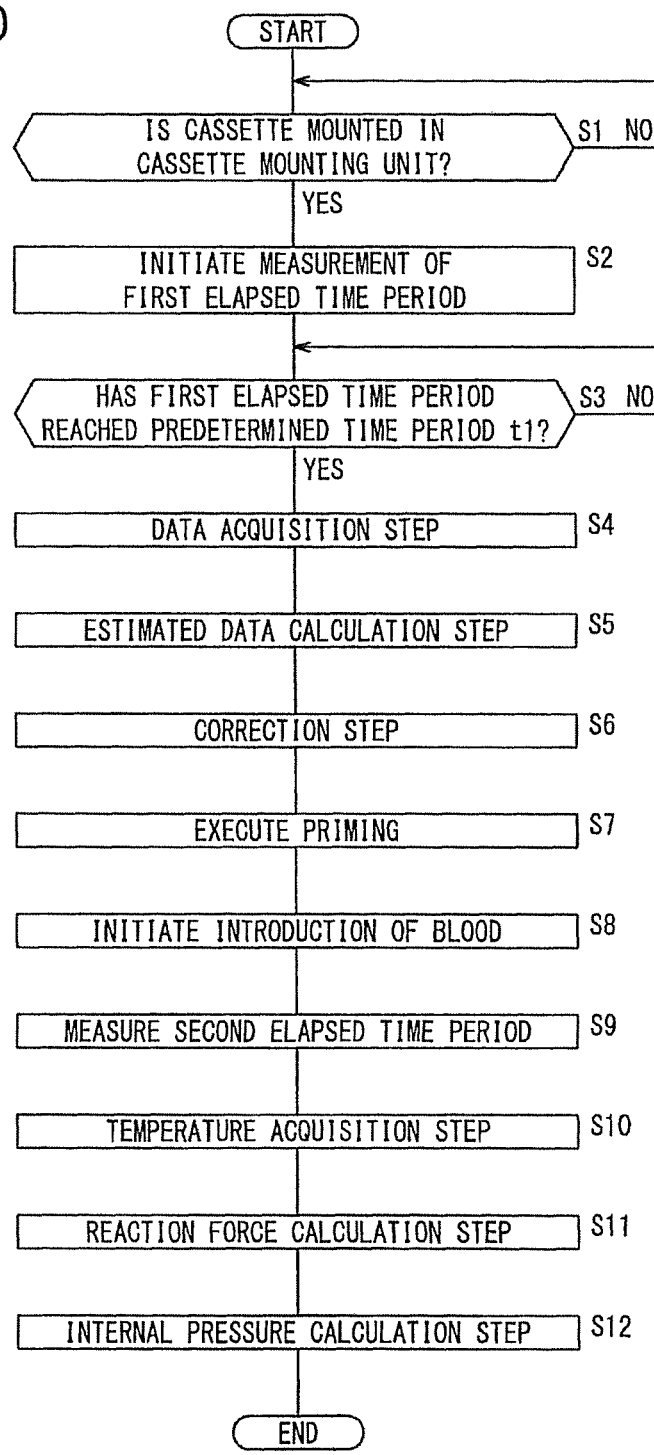
FIG. 10 is a flowchart for describing a circuit internal pressure acquisition method according to an embodiment of the present invention.

In step S1 of FIG. 10, the control unit 102 determines whether or not the cassette 28 has been mounted in the cassette mounting unit 78. More specifically, the control unit 102 determines that the cassette 28 has been mounted in the cassette mounting unit 78 when the lid 86 is closed, in a state in which the cassette 28 is mounted in the cassette mounting groove 82 of the attachment base 84.

If the control unit 102 determines that the cassette 28 is not mounted in the cassette mounting unit 78 (step S1: NO), the control unit 102 remains at step S1 until it is determined that the cassette 28 has been mounted in the cassette mounting unit 78.

In the case that the control unit 102 determines that the cassette 28 has been mounted in the cassette mounting unit 78 (step S1: YES), then in step S2, the control unit 102 initiates measurement of a first elapsed time period from when the control unit 102 determines that the cassette 28 has been mounted in the cassette mounting unit 78. Subsequently, in step S3, the control unit 102 determines whether or not the first elapsed time period has reached the predetermined time period t1 (see FIG. 11). In this instance, although the predetermined time period t1 can be arbitrarily set, the predetermined time period t1 may be set to five minutes, for example.

If the control unit 102 determines that the first elapsed time period has not reached the predetermined time period t1 (step S3: NO), the process remains at step S3 until it is determined that the first elapsed time period has reached the predetermined time period t1. In the case that the control unit 102 determines that the first elapsed time period has reached the predetermined time period t1 (step S3: YES), then in step S4, a data acquisition step is performed.

As shown in FIG. 11, in the data acquisition step, before collection of blood components is performed, the data acquisition unit 106, using the load detected by the first load detecting unit 88 during a predetermined data acquisition time period t2, acquires the initial data A indicative of the temporal change in the reaction force of the first applied load measurement unit 60. In this instance, although the predetermined time period t2 can be arbitrarily set, the predetermined time period t2 may be set to five minutes, for example.

Subsequently, in step S5 of FIG. 10, an estimated data calculation step is performed. As shown in FIG. 11, in the estimated data calculation step, on the basis of the initial data A, the estimated data calculation unit 112 calculates estimated data B (a baseline) for the purpose of estimating the reaction force of the first load detecting unit 88 that changes depending on the time period during which the blood components are collected. More specifically, the estimated data calculation unit 112 calculates the estimated data B using the results obtained using a least squares method based on the initial data A, and a correction variable that is a function of temperature. The correction variable can be acquired in advance by experiment or analysis. Consequently, it is possible to accurately calculate the reaction force of the first applied load measurement unit 60 in real time, which changes depending on the time period during which the blood components are collected. The calculated estimated data B is saved (stored) in the storage unit 104.

However, in the estimated data calculation step, the estimated data B calculated by the estimated data calculation unit 112 need not necessarily include a correction variable that is a function of temperature. In this case, it is also possible to eliminate the temperature acquisition step of step S10 which will be described later.

Figure 12:
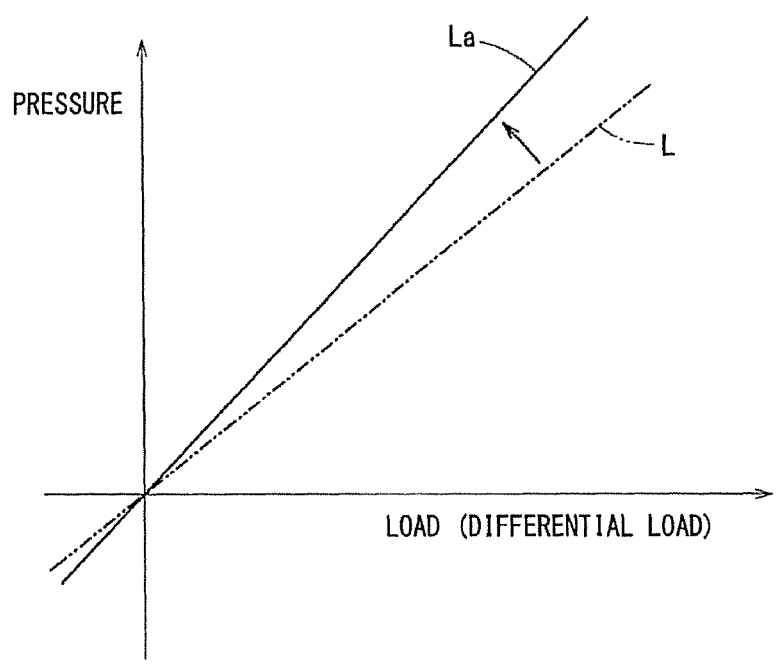
FIG. 12 is a graph for describing a correction to the slope of a calibration curve.

Next, in the correction step of step S6, the slope of the calibration curve L (see FIG. 12), which is data that is used for calculating the internal pressure, is corrected using the load detected by the second load detecting unit 90. Consequently, a calibration curve La, the slope of which has been corrected, is obtained. The calibration curve L can be acquired in advance by experiment or analysis.

Since the second applied load measurement unit 62 is more easily deformed than the first applied load measurement unit 60, the relationship between the load detected by the second load detecting unit 90 and the pressure corresponding to the load is extremely stable. Accordingly, by using the second load detecting unit 90 as a reference sensor for the first load detecting unit 88, and thereby correcting the slope of the calibration curve L used when calculating the circuit internal pressure in the correction step, it is possible to measure the circuit internal pressure with high accuracy.

The correction step may be performed (between step S2 and step S3) until the first elapsed time period reaches the predetermined time period t1. In this case, it is possible to shorten the preparation time until blood component collection is started.

Subsequently, in step S7 of FIG. 10, the ACD solution transfer pump 98 is driven, and carries out the aforementioned priming in which the ACD solution is filled until immediately before the blood line 42 of the cassette 28. Thereafter, in step S8, blood is introduced into the blood line 42 of the cassette 28. At this time, in step S9, the control unit 102 starts to measure the second elapsed time period from the start of flow of blood in the blood collection line 42a.

Subsequently, in the temperature acquisition step (information acquisition step) of step S10, the temperature acquisition unit 110 calculates the temperature of the line forming member 53 (first applied load measurement unit 60) on the basis of the second elapsed time period and the time and temperature curve (temperature calculation data). The time and temperature curve is data indicative of a relationship between the second elapsed time period since the start of introduction of blood into the blood line 42 and the temperature of the line forming member 53, and such data is saved (stored) in the storage unit 104. The time and temperature curve can be acquired in advance by experiment or analysis.

Moreover, in the temperature acquisition step, an external database may be accessed in which the time and temperature curve is stored, and the time and temperature curve may be referred to. Further, in the temperature acquisition step, the temperature of the line forming member 53 (temperature of the wall portion of the blood line 42) may be acquired using a non-illustrated temperature sensor.

Thereafter, in the reaction force calculation step of step S11, during collection of the blood components, the reaction force calculation unit 116 calculates the reaction force of the first applied load measurement unit 60 based on the estimated data B. More specifically, the reaction force is calculated by substituting the temperature of the first applied load measurement unit 60 acquired in the temperature acquisition step, and the first elapsed time period into the calculation formula for the estimated data B.

In addition, in the internal pressure calculation step of step S12, during collection of the blood components, the internal pressure calculation unit 118 calculates a differential load, which is obtained by subtracting the reaction force calculated in the reaction force calculation step from the load detected by the first load detecting unit 88, and calculates the internal pressure (circuit internal pressure) of the first applied load measurement unit 60 on the basis of the differential load and the calibration curve La, the slope of which has been corrected.

In this case, the blood component collection system 10 and the circuit internal pressure acquisition method according to the present embodiment exhibit the following effects.

Figure 13A:
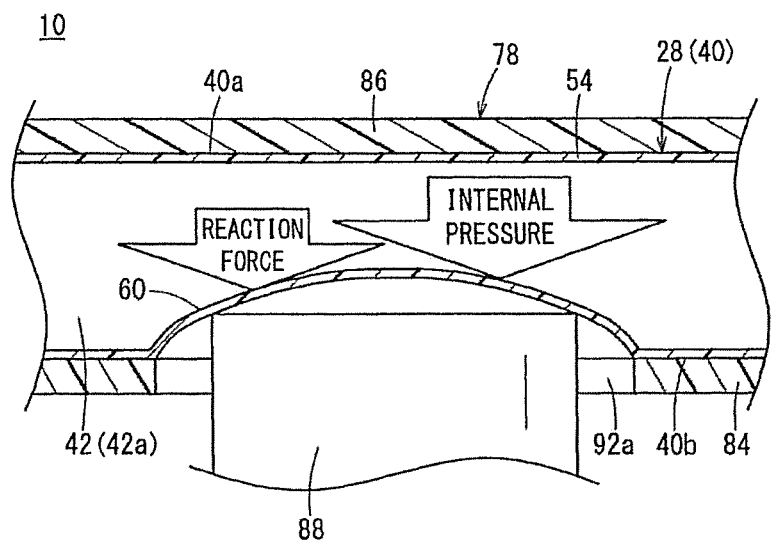
FIG. 13A is a diagram for describing load detection at a positive pressure.
Figure 13B:
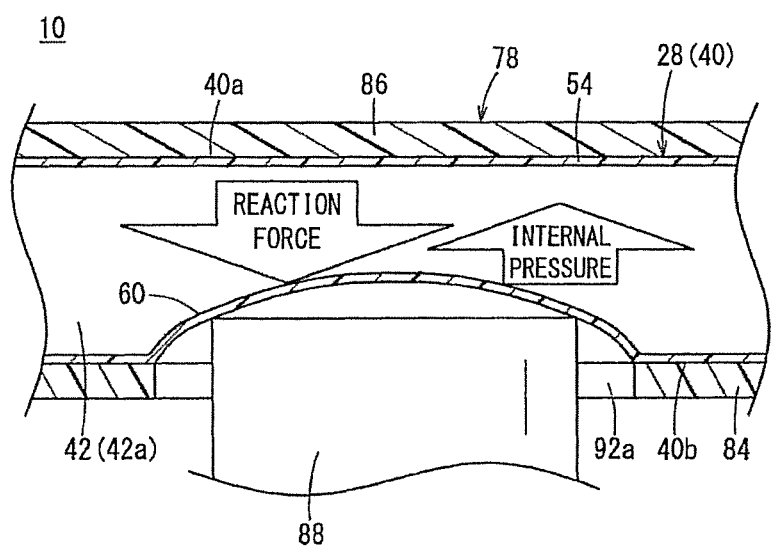
FIG. 13B is a diagram for describing load detection at a negative pressure.

In the case that the collection and returning pump 100 is in operation during blood component collection (during a blood collection operation or during a blood returning operation), by the first load detecting unit 88, a load is detected which is the sum of the internal pressure (circuit internal pressure) of the blood collection line 42a through which the blood flows, and the reaction force of the first applied load measurement unit 60 (a restorative force accompanying deformation of the first applied load measurement unit 60). That is, in the case that the circuit internal pressure is a positive pressure, as shown in FIG. 13A, the load detected by the first load detecting unit 88 (the pressing force from the first applied load measurement unit 60) is obtained simply by adding the circuit internal pressure and the reaction force. On the other hand, in the case that the circuit internal pressure is a negative pressure, as shown in FIG. 13B, the load detected by the first load detecting unit 88 is obtained simply by subtracting the absolute value of the circuit internal pressure from the reaction force.

Figure 14:
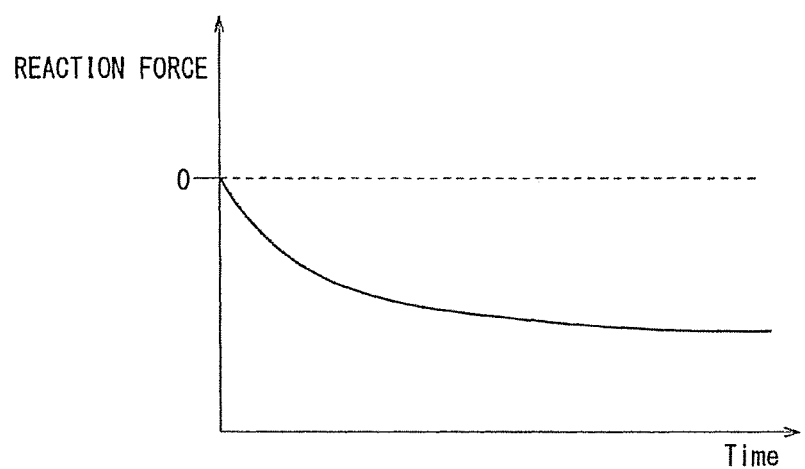
FIG. 14 is a diagram for describing a timewise change in a reaction force.

However, as shown in FIG. 14, the reaction force of the first applied load measurement unit 60 decreases over time. In FIG. 14, an image is shown of a temporal change in the reaction force of the first applied load measurement unit 60 in the case that the reaction force of the first applied load measurement unit 60 when the cassette 28 is mounted in the cassette mounting unit 78 is set to zero. The reason that the reaction force of the first applied load measurement unit 60 decreases over time in the foregoing manner is due to the fact that creep is generated accompanying continuation of a state in which the first applied load measurement unit 60 is pressed by the first load detecting unit 88. Accordingly, when a fixed value that does not change over time is used as the reaction force of the first applied load measurement unit 60, the measurement accuracy of the internal pressure of the first applied load measurement unit 60 is lowered.

Thus, the blood component collection system 10 is equipped with the data acquisition unit 106, the estimated data calculation unit 112, the reaction force calculation unit 116, and the internal pressure calculation unit 118. In addition, before collection of blood components is carried out in the cassette attached state, the data acquisition unit 106 acquires the initial data A which is indicative of a temporal change in the reaction force of the first applied load measurement unit 60. On the basis of the initial data A, the estimated data calculation unit 112 calculates the estimated data B for the purpose of estimating the reaction force of the first applied load measurement unit 60 during collection of the blood components. During collection of the blood components, the reaction force calculation unit 116 calculates the reaction force of the first applied load measurement unit 60 based on the estimated data B. The internal pressure calculation unit 118 calculates the internal pressure (circuit internal pressure) of the first applied load measurement unit 60, on the basis of the reaction force calculated by the reaction force calculation unit 116, and the load detected by the first load detecting unit 88.

Consequently, since based on the estimated data B it is possible to calculate the reaction force of the first applied load measurement unit 60 during collection of the biological components, which changes with the passage of time, it is possible for the circuit internal pressure to be accurately measured. The circuit internal pressure, for example, ranges from −300 mmHg to 500 mmHg.

Immediately after the biological component collection device (cassette 28) is mounted in the separation device (centrifugal separation device 14), the applied load measurement unit (first applied load measurement unit 60) undergoes creep deformation to a comparatively large extent, and therefore, the reaction force of the applied load measurement unit (first applied load measurement unit 60) easily fluctuates. However, the data acquisition unit 106 acquires the initial data A during the data acquisition time period t2 after the elapse of the predetermined time period t1 from when the biological component collection device (cassette 28) was mounted in the separation device (centrifugal separation device 14). Therefore, the accuracy of the estimated data B can be improved.

The estimated data calculation unit 112 calculates the estimated data B using a least squares method based on the initial data A. Consequently, it is possible to easily calculate the estimated data B.

The separation device (centrifugal separation device 14) includes the attachment base 84 to which the biological component collection device (cassette 28) is attached, and the lid 86 adapted to retain the biological component collection device (cassette 28) with respect to the attachment base 84. The biological component collection device (cassette 28) is attached to the separation device (centrifugal separation device 14) by closing the lid 86, in a state in which the biological component collection device (cassette 28) is attached to the attachment base 84. In accordance with this feature, the biological component collection device (cassette 28) can easily be attached with respect to the separation device (centrifugal separation device 14).

The biological component collection device is not limited to being in the form of the cassette 28. Accordingly, the biological component collection device may be equipped with a first soft tube member having the blood collection line 42a, and a second soft tube member having the blood returning line 42b, and may be constituted in a manner so that both end portions of the first soft tube member and the second soft tube member are connected together respectively via connectors.

The internal pressure calculation data that is used when calculating the circuit internal pressure using the load detected by the first load detecting unit 88 is not limited to the calibration curve L, but may be a table that is prepared beforehand. The first load detecting unit 88 and the second load detecting unit 90 may be configured in a manner so as to measure the load (in a non-contact manner) without applying pressure to the first applied load measurement unit 60 and the second applied load measurement unit 62.

The influence information that is acquired by the information acquisition unit is not limited to the temperature of the line forming member 53, but may be an elapsed time period from flowing of the biological liquid through the biological liquid line (blood line 42) or a hardness of the line forming member 53 (first applied load measurement unit 60).

The scope of application of the present invention is not limited to a blood component collection system 10, but may be applied to various systems through which a liquid is made to flow through a flow path, for example, a whole blood donation system, or a culture apparatus for various types of cells which are collected or cultured from patients or donors, or alternatively, a medicinal solution administration system, or the like. Accordingly, the liquid that flows in the biological component collection device (biological component collection system) is not limited to blood.

The biological component collection system and the circuit internal pressure acquisition method according to the present invention are not limited to the above-described embodiments, and it goes without saying that various modifications could be adopted therein within a range that does not depart from the essence and gist of the present invention.

DESCRIPTION OF REFERENCE CHARACTERS

10 . . . blood component collection system (biological component collection system)

14 ... centrifugal separation device (separation device)
28 ... blood component collection cassette (biological component collection device)
42 ... blood line (biological fluid line)
53 ... line forming member
60 ... first applied load measurement unit (applied load measurement unit)
88 ... first load detecting unit (load detecting unit)
106 ... data acquisition unit
112 ... estimated data calculation unit
116 ... reaction force calculation unit
118 ... internal pressure calculation unit
A ... initial data
B ... estimated data

The invention claimed is:

1. A circuit internal pressure acquisition method using a biological component collection system equipped with a separation device adapted to separate a biological component from a biological liquid, and a biological component collection device configured to be attachable to the separation device and collect a desired biological component from the biological liquid;
    wherein the biological component collection device is formed of a soft material and has a line forming member defining a biological liquid line to allow the biological liquid or the biological component to flow therein;
    the separation device comprising a load detecting unit adapted to detect a load applied to an applied load measurement unit which partially makes up the line forming member in an attached state in which the biological component collection device is attached to the separation device;
    the circuit internal acquisition method comprising:
    a data acquisition step of acquiring, before the biological liquid or the biological component is made to flow through the biological liquid line for biological component collection, initial data indicative of a timewise change in a reaction force of the applied load measurement unit using the load detected by the applied load detecting unit in the device installed state;
    an estimated data calculation step of calculating, on the basis of the initial data, estimated data for estimating the reaction force of the applied load measurement unit which changes over time during collection of the biological component;
    a reaction force calculation step of calculating, during collection of the biological component, the reaction force on the basis of the estimated data; and
    an internal pressure calculation step of calculating an internal pressure of the applied load measurement unit, on the basis of the reaction force the load detected by the applied load detecting unit.

2. The circuit internal pressure acquisition method according to claim 1, wherein, in the data acquisition step, the initial data is acquired during a predetermined data acquisition time period, after a predetermined time period has elapsed from when the biological component collection device was mounted in the separation device.

3. The circuit internal pressure acquisition method according to claim 2, wherein, in the estimated data calculation step, the estimated data is calculated using a least squares method based on the initial data.

4. The circuit internal pressure acquisition method according to claim 1, wherein, in the estimated data calculation step, the estimated data is calculated using a least squares method based on the initial data.

* * * * *

UNITED STATES PATENT AND TRADEMARK OFFICE
CERTIFICATE OF CORRECTION

PATENT NO. : 10,758,664 B2  
APPLICATION NO. : 16/668572  
DATED : September 1, 2020  
INVENTOR(S) : Masatsugu Igarashi and Davis Benz Page 1 of 1

It is certified that error appears in the above-identified patent and that said Letters Patent is hereby corrected as shown below:

On the Title Page

Inventor's name:
David BENZ

Should read:
Davis BENZ

Signed and Sealed this
Seventeenth Day of November, 2020

Andrei Iancu
*Director of the United States Patent and Trademark Office*